United States Patent [19]

Barcan

[11] 4,042,109
[45] Aug. 16, 1977

[54] MEDICAL PROCEDURE PACKAGE

[75] Inventor: Donald S. Barcan, Union, N.J.

[73] Assignee: C. R. Bard, Inc., Murray Hill, N.J.

[21] Appl. No.: 651,881

[22] Filed: Jan. 21, 1976

[51] Int. Cl.² .................. B65D 1/34; B65D 85/00; A61B 19/02
[52] U.S. Cl. .................................................. 206/440
[58] Field of Search ............... 206/440, 438, 229, 494; 128/132 D; 283/34, 35

[56] References Cited
U.S. PATENT DOCUMENTS

| | | | |
|---|---|---|---|
| 3,137,387 | 6/1964 | Overment | 206/229 |
| 3,770,119 | 11/1973 | Hultberg et al. | 206/440 |
| 3,881,476 | 5/1975 | Bolker et al. | 128/132 D |

*Primary Examiner*—William T. Dixson, Jr.

[57] ABSTRACT

A medical procedure tray incorporating a stepped rim defining inner and outer ledges peripherally thereabout. A surgical sheet or drape includes an aperture formed therethrough conforming to the tray area within the inner ledge with the drape, about the aperture, being affixed to the inner ledge for a folding of the drape inwardly onto the inner ledge and inward of the outer ledge which subsequently receives a package sealing cover sheet. The drape includes diametrically opposed corners defining gripping tabs which, through a transverse and longitudinal fan folding of the drape, remain continuously upwardly exposed and accessible for a grasping thereof and a single motion complete unfolding of the drape upwardly and out of the tray in surrounding relation thereto.

26 Claims, 11 Drawing Figures

U.S. Patent    Aug. 16, 1977    Sheet 1 of 3    4,042,109
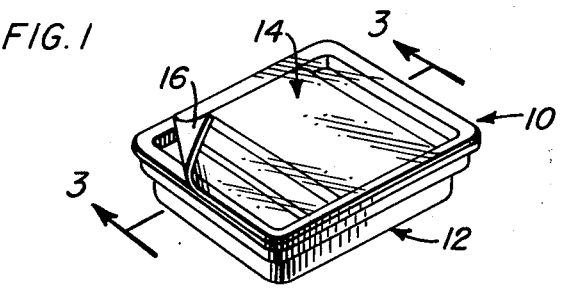
FIG. 1
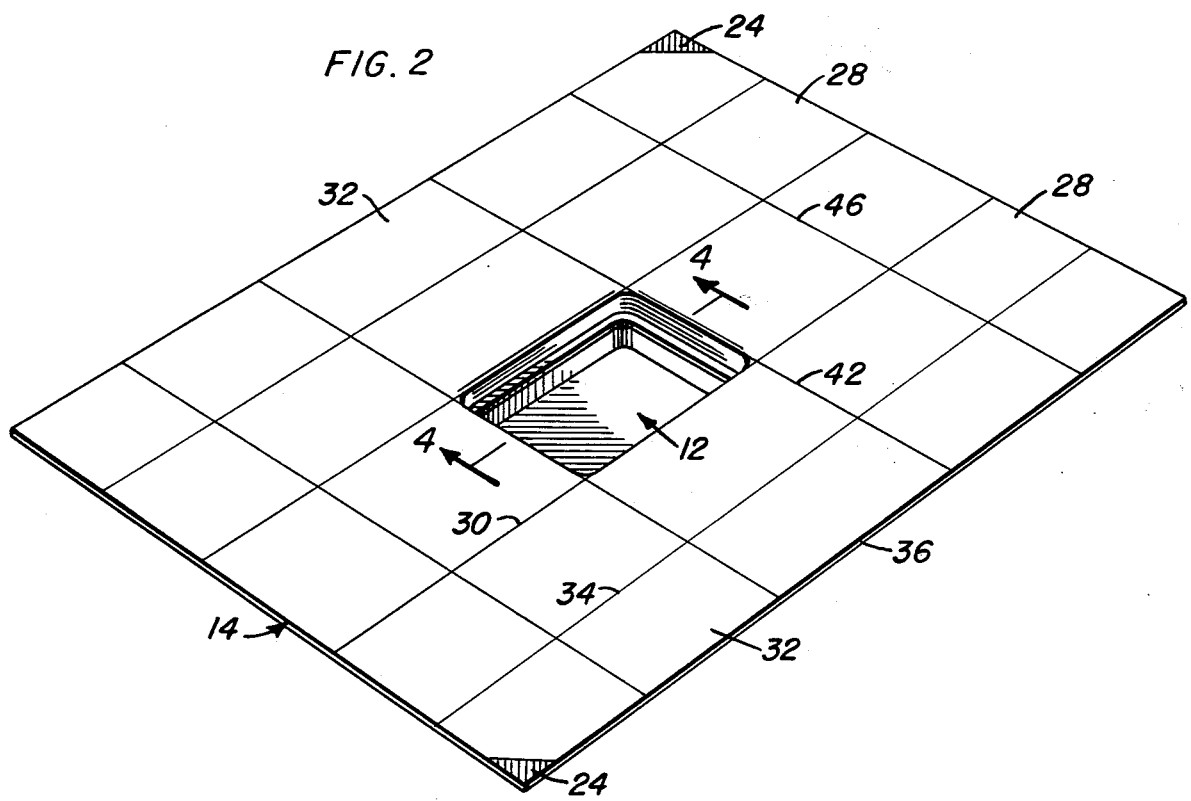
FIG. 2
FIG. 3
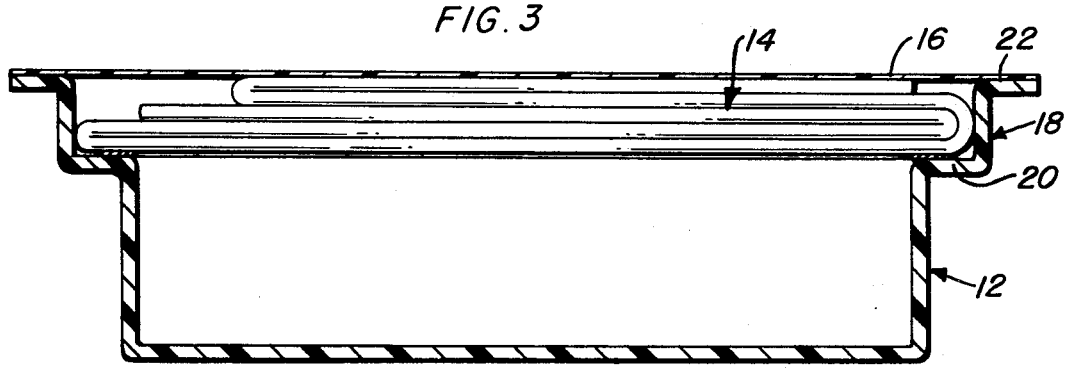

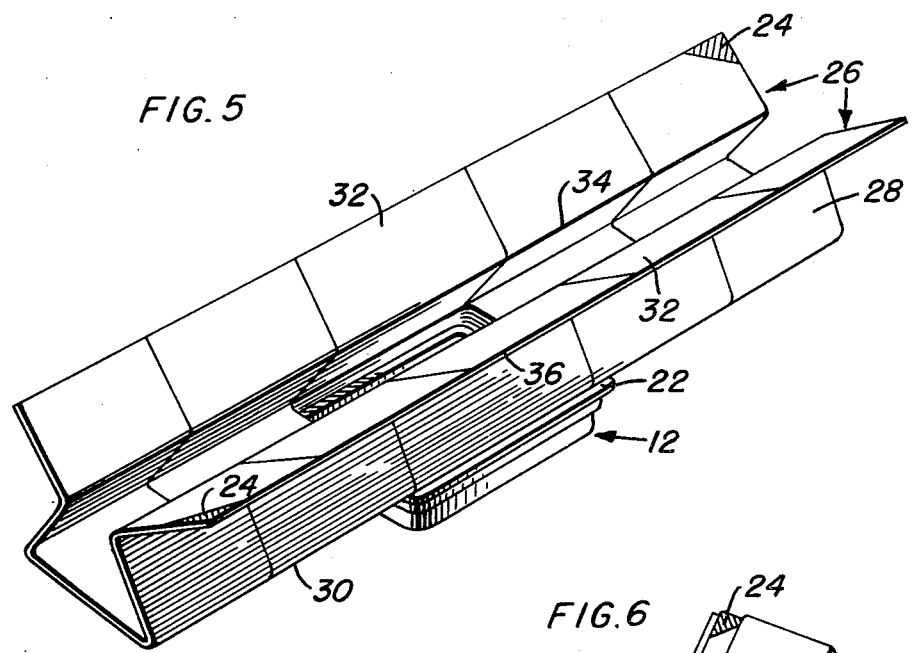
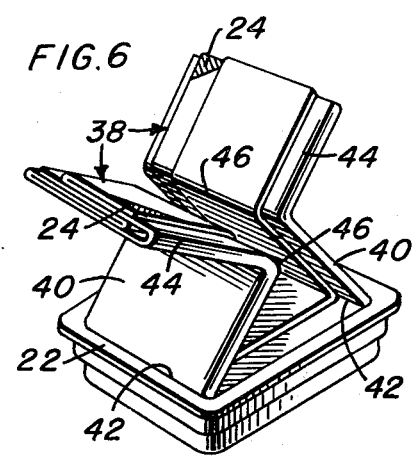
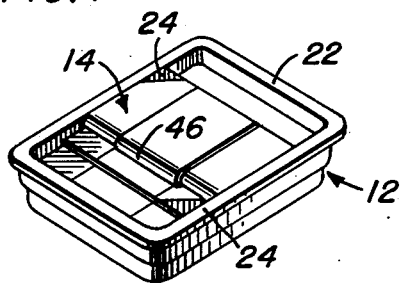
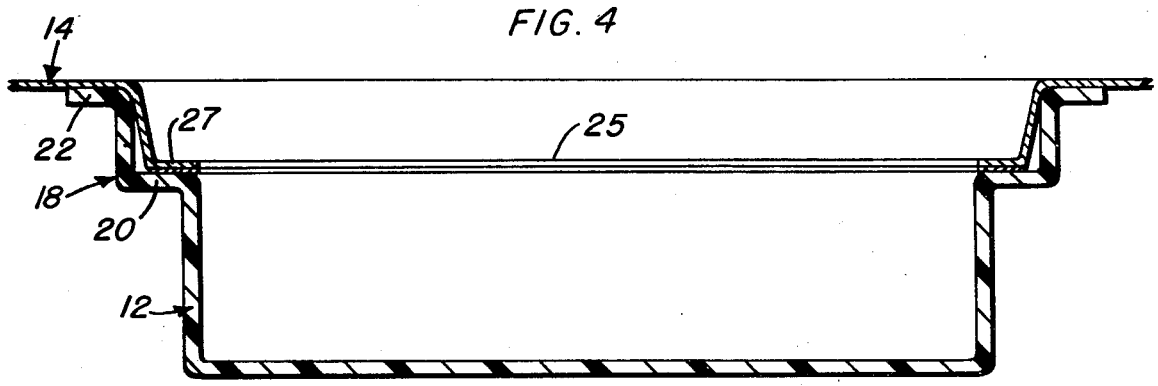

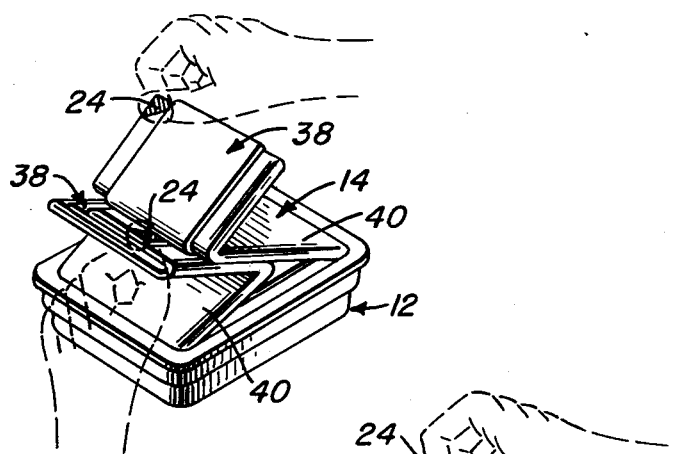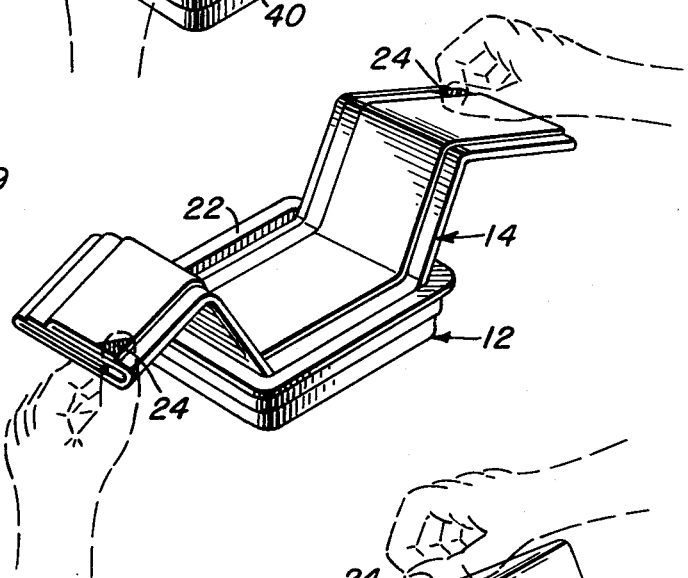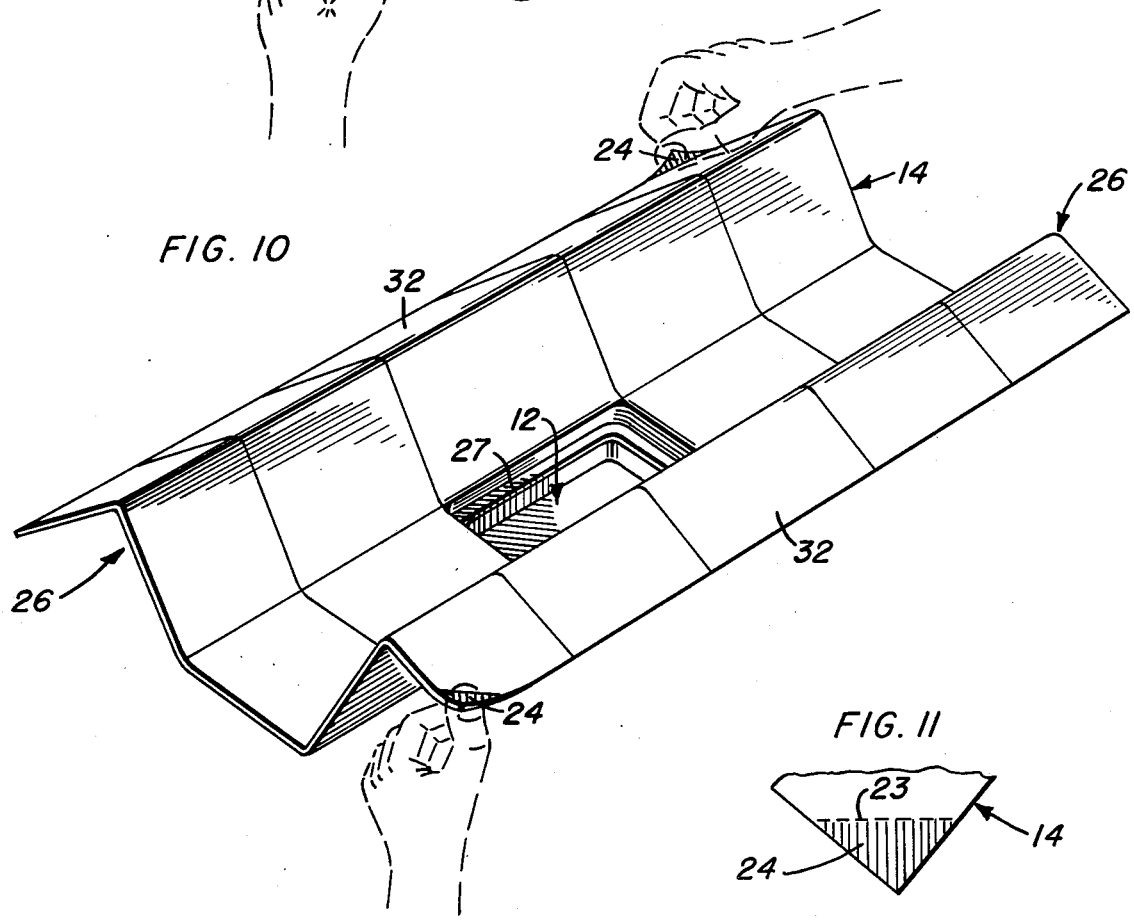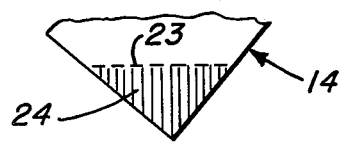

MEDICAL PROCEDURE PACKAGE

The invention herein relates to medical procedure packages of the type wherein a supply and/or equipment tray is provided with a sterile field defining sheet or drape, normally folded so as to define a compact package within an appropriate protective enclosure so as to constitute a pre-packaged, single use item.

Such items, after packaging, are sterilized and stored until needed. When needed, the package, ideally, is opened and the drape or sheet spread in a manner so as to form an upper sterile field adjacent the exposed and still sterile tray interior. It is in this area in particular that problems arise with regard to known equipment. More specifically, prior to the invention disclosed herein, the manipulation of the folded sheet or drape to effect a complete spreading thereof so as to define the field required an excessive handling of the sheet which was both time consuming and awkward, and more importantly, tended to affect or destroy the sterile nature of a good portion of the field.

The following constitute the known prior art:

| | | | |
|---|---|---|---|
| 1,110,051 | Harpster | 3,481,462 | Chapel |
| 2,933,431 | Sperouleas | 3,520,401 | Richter et al |
| 2,985,288 | Reich | 3,527,400 | Shepherd et al |
| 3,032,186 | Jenkins | 3,604,616 | Greif |
| 3,061,087 | Scrivens et al | 3,650,393 | Reiss et al |
| 3,070,225 | Schwartz | 3,690,315 | Chittenden et al |
| 3,104,012 | Beamish | 3,730,338 | Chesky |
| 3,329,261 | Serany et al | 3,770,119 | Hultberg et al |
| 3,343,534 | Keoughan et al | 3,780,857 | Rosano et al |
| 3,361,253 | Lonholdt | 3,795,309 | Link |
| 3,403,776 | Denny | 3,797,652 | Chesky |
| 3,410,393 | Lee | 3,802,555 | Grasty et al |
| 3,419,136 | Pratt | 2,990,948 | Zackheim |
| | | 3,137,387 | Overment |

The invention herein is specifically concerned with a unique manner of compactly packaging the sterile field defining sheet or drape directly within the upper portion of the equipment tray while at the same time providing for a single motion manipulation of the sheet to effect a complete longitudinal and transverse expansion thereof to its full field forming position.

Basically, the primary objects of the invention are to provide compact packaging of combined medical procedure trays and drapes in conjunction with means for effecting a substantially instantaneous setup of the tray and surrounding field in a manner which maintains the sterile nature of the field and tray to a degree not heretofore possible.

In effecting what are considered to be significant advances in the area of medical procedure packaging, the package herein utilizes a tray provided with a stepped rim peripherally thereabout and a foldable sheet or drape affixed peripherally about the inner step or ledge of the tray rim and projecting outwardly therefrom. The drape is provided with an opening immediately inward of the step affixed portion so as to allow direct access to the interior of the tray.

A pair of diametrically opposed corners of the normally rectangular drape define handling or manipulating tabs which constitute the only areas with which contact is required so as to effect a complete unfolding of the drape about the tray. In order to provide for a single motion complete unfolding of the drape, a first pair of opposed side sections, each including, at an outer corner thereof, one of the tabs, are fan folded inward so as to overlie the inner step of the tray at the corresponding sides thereof with the relationship of the opposed fan folds being such so as to maintain both tabs upwardly exposed. The opposed ends of the two fan folds, normally projecting longitudinally beyond the second pair of sides of the tray, are also then inwardly fan folded so as to overlie the inner tray rim step and fall completely within the confines of the tray. The relationship between the two second fan folds are such so as to maintain the tabs upwardly exposed and accessible at diametrically opposed corners of the tray adjacent the outer step or ledge thereof with the completely folded drape being received within the rim between the inner and outer steps whereby a subsequent closing of the package can be effected by a cover peripherally secured to the outer step or ledge.

Packaged in this manner, the field can be quickly, accurately and safely formed by merely stripping away the cover, grasping the two tab corners, and effecting a single diametric spreading of the corners which results in a full longitudinal and transverse unfolding of the sheet. Any contact with the upper ledge of the tray in obtaining access to the tabs will not affect the sterile nature thereof in that the expanded sheet will overlie and protectively cover this upper ledge. Further, the portion of the folded sheet directly underlying the tabs, and thus also possibly being contacted, are, in the unfolded sheet, a portion of the undersurface thereof and not the upper sterile field.

The particular objects and advantages of the invention, together with others which will become subsequently apparent, reside in the details of construction and manner of use as more fully hereinafter described and claimed. Reference is made to the accompanying drawings forming a part hereof, wherein like numerals refer to like parts throughout, and in which:

FIG. 1 is a perspective view of the medical procedure package of the present invention with a portion of the cover thereof peeled back;

FIG. 2 is a perspective view of the medical procedure package in its fully open "in use" position;

FIG. 3 is an enlarged cross-sectional view taken through the package substantially on a plane indicated by line 3—3 in FIG. 1;

FIG. 4 is an enlarged cross-sectional detail taken substantially on a plane passing along line 4—4 in FIG. 2;

FIG. 5 is a perspective view illustrating an initial step in folding the drape;

FIG. 6 is a perspective view illustrating a subsequent step in folding the drape into the tray;

FIG. 7 is a perspective view illustrating the package with the drape completely folded with the tray;

FIG. 8 illustrates an initial position of the drape in the single motion unfolding thereof;

FIG. 9 illustrates a further position of the drape in the unfolding thereof;

FIG. 10 illustrates a position of the drape immediately prior to assuming its completely unfolded position or orientation as illustrated in FIG. 2; and FIG. 11 is a variation wherein the tab is selectively removable.

Referring now more specifically to the drawings, the medical procedure package is generally designated by a reference numeral 10 and basically comprises a tray 12, the drape 14 foldable within the tray, and a cover 16 enclosing the tray with the drape therein.

The tray 12, preferably of plastic, while normally of a generally rectangular configuration, can be of any desired geometric configuration, in each case being of a depth, below the rim portion 18, sufficient so as to accomodate the various supplies and equipment to be stored therein. The rim portion 18, which extends peripherally about the tray, is stepped, including an inner step or ledge 20 surrounding the main tray compartment immediately thereabove, and an upper and outer step or ledge 22 constituting a peripheral flange to which the cover 16 is sealed. The vertical spacing between the inner and outer steps 20 and 22, noting FIGS. 3 and 7 in particular, is of a size so as to completely and closely accomodate the folded drape 14.

The drape 14, unfolded and providing a sterile field as illustrated in FIG. 2, will normally be rectangular with the tray 12 preferably centrally located thereto. A pair of opposed corners 24 constitute gripping tabs by which a single movement unfolding of the drape 14 is to be effected. For purposes of convenience, these corner tabs 24 can be provided with visable indicia, coloring or the like. Also, a line of perforations 23, as suggested in FIG. 11, can be provided for removal of each tab 24 from the drape 14 after opening, if procedure dictates. Alternately, the tabs can be adhesively secured to the drape for ease of removal.

The sheet or drape 14 will normally be a sheet of "CSR wrap" (CSR standing for "Central Supply Room") which may be muslin or "Dennison wrap" or some other suitable woven or non-woven material.

An opening or aperture 25, conforming in size to the main tray compartment, is aligned therewith. The peripheral portion 27 of the drape 14 immediately surrounding the aperture 25 is sealed to the inner step of ledge 20 completely thereabout by adhesive or other appropriate means. This constitutes the only area of direct bonding of the drape 14 to the tray 12 with the drape extending, in its unfolded position, outwardly from the sealed engagement to the ledge 20 in free overlying relationship to the vertical wall of the rim and the surrounding outer step or ledge 22. In this manner, the sheet or drape 14 is freely movable between the unfolded position of FIG. 2 to a position, as best noted in FIGS. 3 and 7, completely collapsed within the rim portion 18 of the tray 12.

As previously indicated, it is a primary intention of the invention to provide for a rapid, direct and positive opening of the folded drape through a single motion, requiring only the one time grasping of the opposed corners of the drape. In order to effect this, and as will be readily appreciated from the folding sequence of FIGS. 5, 6 and 7, and the unfolding sequence of FIGS. 8, 9 and 10, the opposed tab forming corners 24 are at all times upwardly exposed and readily accessible. This is provided for by the utilization of a particular folding sequence. In regard thereto, attention is initially directed to FIGS. 2 and 5 wherein it is noted that a first pair of opposed sides, which for purposes of description shall be indicated as the longitudinally extending sides, are fan folded inward so as to each overlie the tray inward of the outer ledge 22 of the corresponding sides of the tray. The two fan folds 26, thus defined, include an intermediate section 28 folded upwardly and inwardly about a first fold line 30, either visibly designated or not, which is so oriented as to allow for a positioning of the formed fold immediately inward of the vertical wall of the rim and on the inner ledge or step 20. The corresponding longitudinally extending outer side section 32 is at the same time folded, about a second fold line 34, outwardly so as to overlie the now upwardly directed surface of the intermediate section or fold 28 with the extreme outer edge 36, and the associated corner defining gripping tab 24, maintaining its basic upward and outward orientation. As will be appreciated, each of the side edges 36 will be, when folded, within the confines of the tray rim 18. Further, while the two fan folds 26 have been illustrated as overlapping, the spatial relationship therebetween can, depending upon the relative sizes of the sheet 14 and tray 12, abut each other or possibly not even contact each other while still being within the confines of the tray. The only criteria is that the overlapping of the fan folds 26 not be such so as to cover or conceal either of the corner tabs 24.

Upon the formation of the two fan folds 26, defining stacks of parallel overlying folds, the fan folds 26 will, in most instances, project longitudinally beyond the second pair of opposed tray sides. With reference in particular to FIGS. 6 and 7, these projecting portions are in turn fan folded inward to define a second pair of fan folds 38. Each of the fan folds 38 include an intermediate section 40 folded upward and inward about a fold line 42 which, for purposes of illustration in FIGS. 2, 5 and 10, has been designated as extending completely across the extent of the sheet or drape 14. This fold line 42, in connection with each of the fan folds 38, is oriented immediately inward of the vertical wall of the rim 18 of the tray 12 so as to, upon a folding, fall completely within the confines of the rim portion of the tray. The outer end section 44 of each fan fold 38 is in turn outwardly folded, about fold line 46, to overlie the now upwardly directed surface of the intermediate section 40. As will be noted, the length of each of these end sections is such so as to fall completely within the confines of the rim area 18 of the tray 12 with the fan folds 38 either overlapping or being coplanar. In every instance, the corner defining gripping tabs 24 remain generally diametrically opposed and upwardly exposed for a direct access thereto.

Folded in the above manner, the stacked folds are positioned immediately below the plane of the upper step or ledge 22. As the final step in forming the package, a contamination-impermeable cover or cover sheet 16 is releasably sealed to the outer step or ledge 22 peripherally thereabout to aseptically enclose the drape and tray interior. This cover may be gas permeable for use in gas sterilization techniques or gas impermeable for other sterilization techniques, such as irradiation. The package 10 is then sterilized in an appropriate manner and stored until such time as needed.

When use of the package is required, the cover 16 is peeled therefrom as suggested in FIG. 1 and the drape 14 quickly and conveniently opened by a single motion. In connection therewith, attention is directed to FIGS. 8, 9, and 10. Basically, the unfolding of the drape or sheet 14 requires only a grasping of the exposed corner tabs 24 and a drawing of the two tabs 24 diametrically outward relative to each other which in turn automatically longitudinally extends the second fan fold 38 and subsequently transversely extends the first fan folds 26 without any crimping, catching or tearing of the drape and in a manner whereby tension is applied both longitudinally and transversely on the unfolded drape so as to insure a complete planar positioning thereof about the tray 12. As indicated, this is quickly and efficiently effected by a grasping of the drape at only two points and a single outward motion by the gripping hands. Incidentally, it will be noted that a gripping of the corner tabs 24 does not bring the hand in contact with any other area of the upper sterile field of the drape in that the tabs directly overlie fold surfaces which will ultimately constitute the under surface of the field and are positioned adjacent the upper tray ledges 22 which will ultimately be covered by the unfolded drape. As a final step, the tabs can be removed from the drape as suggested in FIG. 11.

From the foregoing, it is to be appreciated that significant advances have been made with regard to medical procedure packages, the manner of forming such packages, and the manner in which such packages are opened and put into use. In conjunction therewith, it is to be appreciated that the foregoing is considered illustrative only of the principles of the invention. Further, since modification and changes may occur to those skilled in the art, for example an off center orientation of the tray relative to the field while still maintaining the basic fan folding manner of collapsing and expanding the field into the tray, it is not desired to limit the invention to the exact construction and operation shown and described. Accordingly, all suitable modifications and equivalents may be resorted to, falling within the scope of the invention as claimed.

What is claimed is:

1. A medical procedure package comprising a tray and a drape secured to and about said tray, said tray having two pairs of generally opposed sides, said drape including generally diagonally opposed upwardly exposed tabs, said drape having opposed first and second side portions extending from a first pair of opposing sides of the tray and longitudinally beyond the second pair of opposing sides of the tray, one of said tabs appearing on each of said first and second side portions, said first and second side portions being transversely fan foldable to a point inward of the corresponding first pair of sides of the tray and defining longitudinal fan folds positioned within the transverse confines of the first pair of sides and projecting longitudinally beyond the second pair of sides so as to form fan folded end portions, the tabs remaining upwardly exposed at diagonally opposed points longitudinally beyond the second pair of opposed sides and on the fan folded end portions, said end portions being longitudinally fan foldable to a point inward of the corresponding second pair of sides of the tray and defining fan folds positioned within the longitudinal confines of the second pair of sides, said tabs remaining upwardly exposed at diagonally opposed points within the confines of the tray.

2. The medical procedure package of claim 1 wherein said tray includes a stepped rim having an outer periphery and an inner peripheral ledge about the main compartment thereof, said drape being secured to said ledge peripherally thereabout with an aperture defined through said drape within the confines of the ledge to expose the interior of said tray.

3. The medical procedure package of claim 2 wherein said drape, when completely folded, is supported on said inner ledge within and below the outer periphery of the stepped rim.

4. The medical procedure package of claim 3 wherein said first and second side portions, upon a fan folding thereof, overlap each other.

5. The medical procedure package of claim 4 wherein said end portions, upon a fan folding thereof, overlap each other.

6. The medical procedure package of claim 5 including a cover engageable with the outer periphery of the rim for a sealing of the folded drape within the tray.

7. A medical procedure package comprising a tray and a drape secured to said tray, said drape comprising plural sections selectively foldable inwardly over said tray for compact storage and unfoldable relative to said tray defining an upwardly directed sterile field outward of the tray, said tray and drape sections when unfolded including generally diagonally opposed portions defining upwardly exposed manually accessible gripping tabs, said tray and drape sections when folded inwardly over said tray maintaining said tabs in a generally diagonally opposed orientation with said tabs maintained upwardly exposed and manually accessible to enable a direct grasping thereof and an unfolding of the folded drape section relative to said tray by a single outward drawing of the tabs in a generally diagonal direction.

8. The medical procedure package of claim 7 wherein said tray and drape sections in the unfolded position include at least one set of generally diagonally opposed corners, said tabs being generally at said corners.

9. The medical procedure package of claim 8 wherein said corners form said tabs.

10. The medical procedure package of claim 7 wherein said tabs, in the folded position of said drape sections, are positioned immediately adjacent opposed sides of the tray.

11. The medical procedure package of claim 7 wherein said drape sections are fan folded inwardly to overlie said tray.

12. The medical procedure package of claim 7 wherein said drape, in the unfolded position of the sections, includes a first upper surface and a second lower surface, said drape sections including at least a first longitudinally extending side section outward of said tray and having one of said tabs thereon, and a longitudinally extending intermediate section between the tray and said side section, a first fold line defined between the intermediate section and the tray for an upward and inward transverse folding of the intermediate section into overlying relation to the tray and an upwardly exposing of the second surface thereof, and a second fold line defined between the intermediate section and the associated side section for a folding of this side section into overlying relation to the second surface of the intermediate section defining a longitudinally extending fan fold forming a first plurality of longitudinally extending stacked sections overlying said tray with the associated tab upwardly exposed.

13. The medical procedure package of claim 12 wherein said fan fold defines first and second end sections, one end section including said associated upwardly exposed tab, a transversely extending intermediate section between the tray and said one of said end sections, a first fold line defined between the transversely extending intermediate section and the tray for an upward and inward longitudinal folding of the transversely extending intermediate section into overlying relation to the tray and the tray overlying portion of the fan fold, and a second fold line defined between the transversely extending intermediate section and the associated end section for a folding of this end section into overlying relation to the transversely extending intermediate section to define a longitudinally collapsed fan fold overlying said tray with the associated tab upwardly exposed.

14. The medical procedure package of claim 13 including a second longitudinally extending side section, an intermediate section between the tray and the second side section, said second side section including a second one of said tabs, said second side section and associated intermediate section being fan foldable inwardly into overlying relation to the tray and defining a second longitudinally extending fan fold with the associated tab upwardly exposed.

15. The medical procedure package of claim 14 wherein said second longitudinally extending fan fold combines with said first mentioned longitudinally extending fan fold to define said first and second end sections.

16. The medical procedure package of claim 15 including a second transversely extending intermediate section between the tray and the second of said end sections, said second of said end sections including the second of said tabs upwardly exposed, said second transversely extending intermediate section and said second end section being fan foldable inward into overlying relation to the tray and defining a second longitudinally collapsed fan fold with the associated tab upwardly exposed.

17. The medical procedure package of claim 16 wherein said longitudinally collapsed fan folds bring the folded drape section completely within the confines of the tray.

18. The medical procedure package of claim 17 wherein said tray includes a peripheral stepped rim, said rim including a lower inner ledge which receives and supports the folded drape sections, said drape being affixed to said inner ledge.

19. The medical procedure package of claim 18 including cover means engageable with the rim of the tray in overlying relation to the folded drape and tray interior.

20. The medical procedure package of claim 12 including a second longitudinally extending side section having a second one of said tabs thereon, and a second longitudinally extending intermediate section between the tray and the second side section, said second longitudinally extending intermediate section and said second side section being fan foldable inwardly into overlying relation to the tray and defining a second longitudinally extending fan fold with the associated tab upwardly exposed.

21. A method of preparing medical procedure material including the packing of a medical drape within a medical procedure tray, said method comprising the steps of fan folding opposed sides of the drape inwardly toward each other to define elongated stacks of folds longitudinally aligned over the interior of the tray with the outer portion of each of said sides defining the upper fold in each stack and the upper surface of the drape at the outer edge of each of said opposed sides remaining upwardly directed in the upper fold in the fan folded position of the side.

22. The method of claim 21, including the step of fan folding the opposed ends of the elongated stacks of folds inwardly toward each other into the interior of the tray with the outer portion of each stack end defining the upper fold and the upper surface of the outer portion of each stack end remaining upwardly directed in the fan folded position thereof.

23. The method of claim 22 including the steps of sealing a cover to the tray over the folded drape and sterilizing the package.

24. The method of claim 23 including the steps of removing the cover, grasping generally diagonally opposed areas, one on the outer portion of each stack end, and diagonally outwardly drawing said areas in a single motion to effect a complete unfolding of all of said fan folds.

25. The method of claim 22 including the steps of grasping generally diagonally opposed areas, one on the outer portion of each stack end, and diagonally outwardly drawing said areas in a single motion to effect a complete unfolding of all of said fan folds.

26. The method of claim 25 including the step of severing said diagonally opposed areas subsequent to an unfolding of said fan folds.

* * * * *